(12) United States Patent
Bukhary

(10) Patent No.: US 8,376,743 B1
(45) Date of Patent: Feb. 19, 2013

(54) ORAL RETRACTOR

(75) Inventor: Mohammed Taher Bukhary, Riyadh (SA)

(73) Assignee: King Saud University, Riyadh (SA)

( * ) Notice: Subject to any disclaimer, the term of this patent is extended or adjusted under 35 U.S.C. 154(b) by 8 days.

(21) Appl. No.: 13/276,098

(22) Filed: Oct. 18, 2011

(51) Int. Cl.
*A61C 5/14* (2006.01)
*A61B 1/24* (2006.01)

(52) U.S. Cl. ......... 433/140; 600/209; 600/242; 128/859

(58) Field of Classification Search .............. 433/1, 2, 433/19, 42, 68, 69, 93, 20, 21, 15; 600/184–245; D24/135, 152–154, 176–182; 128/845, 846, 128/848, 859–862
See application file for complete search history.

(56) References Cited

U.S. PATENT DOCUMENTS

| | | | | |
|---|---|---|---|---|
| 152,074 A * | 6/1874 | Chevalier | | 433/138 |
| 658,669 A * | 9/1900 | Morrow | | 600/211 |
| 670,397 A * | 3/1901 | Cross | | 24/533 |
| 692,281 A * | 2/1902 | Hare | | 433/93 |
| 735,762 A * | 8/1903 | Hare | | 600/238 |
| 770,853 A * | 9/1904 | Hare | | 600/238 |
| 776,348 A * | 11/1904 | Parsons | | 600/209 |
| 817,659 A * | 4/1906 | McLean | | 600/244 |
| 1,157,565 A * | 10/1915 | Mayer | | 600/242 |
| 1,311,409 A * | 7/1919 | McAlister | | 600/243 |
| 1,388,421 A * | 8/1921 | Forgrave | | 600/239 |
| 1,389,436 A * | 8/1921 | Cameron | | 600/219 |
| 1,420,493 A * | 6/1922 | Moyer | | 600/239 |
| 1,457,824 A * | 6/1923 | De Nise | | 433/179 |
| 1,533,367 A * | 4/1925 | Baylis | | 24/547 |
| 1,727,879 A * | 9/1929 | Hodlick et al. | | 600/219 |
| 1,986,275 A * | 1/1935 | Lowry | | 433/93 |
| 2,275,553 A * | 3/1942 | Piace | | 52/511 |
| 2,535,005 A * | 12/1950 | Wiprud | | 433/138 |
| 2,581,679 A * | 1/1952 | Marshall | | 600/243 |
| 2,651,300 A * | 9/1953 | Fehrman | | 600/244 |
| 2,685,679 A * | 8/1954 | Sam | | 439/835 |
| 2,697,432 A * | 12/1954 | Scinta | | 600/239 |
| 2,776,489 A * | 1/1957 | McGahee | | 433/138 |
| 2,859,519 A * | 11/1958 | Cohn | | 433/93 |
| 2,908,954 A * | 10/1959 | Chaun | | 24/67.9 |

(Continued)

FOREIGN PATENT DOCUMENTS

CH 602090 A5 * 7/1978
DE 3202270 A1 * 8/1983

(Continued)

*Primary Examiner* — Todd Manahan
*Assistant Examiner* — Michael R Ballinger
(74) *Attorney, Agent, or Firm* — Richard C. Litman

(57) ABSTRACT

The oral retractor is provided for retracting at least a portion of a patient's mouth. The oral retractor is formed from single, continuous closed-loop strand of stainless steel wire. The oral retractor includes a superior lip-engaging portion for retracting the patient's upper lip away from the upper teeth and gums, and an inferior lip-engaging portion for retracting the patient's lower lip away from the patient's lower teeth and gums. Bilateral arcuate cheek-engaging portions extend posteriorly from the lip-engaging portions for retracting the patient's cheeks away from the teeth and gums. The lip-engaging portions are formed from linear portions defining tented arches that extend anteriorly, and the superior lip-engaging portion may be canted upward, while the inferior lip-engaging portion may be canted downward. The cheek-engaging portions may be substantially parabolic. The retractor may be substantially symmetrical about planes bisecting the retractor vertically and horizontally.

15 Claims, 5 Drawing Sheets

U.S. PATENT DOCUMENTS

| | | | |
|---|---|---|---|
| 2,937,445 A * | 5/1960 | Erickson | 433/93 |
| 3,241,550 A * | 3/1966 | Gelarie | 600/242 |
| 3,455,024 A * | 7/1969 | Gelarie | 433/93 |
| 4,002,162 A | 1/1977 | Weisser | |
| 4,053,984 A * | 10/1977 | Moss | 433/93 |
| 4,200,089 A * | 4/1980 | Inoue | 600/242 |
| 4,321,916 A * | 3/1982 | McKee | 600/209 |
| D283,158 S * | 3/1986 | Jackson | D24/176 |
| 4,889,490 A * | 12/1989 | Jenkinson | 433/136 |
| 5,165,723 A * | 11/1992 | Evans | 281/42 |
| 5,174,284 A * | 12/1992 | Jackson | 128/200.26 |
| 5,184,604 A * | 2/1993 | Brillante | 600/206 |
| 5,199,872 A * | 4/1993 | Leal | 433/136 |
| 5,340,313 A * | 8/1994 | Hussin | 433/136 |
| 5,441,040 A * | 8/1995 | Williams, Jr. | 600/236 |
| 5,513,634 A * | 5/1996 | Jackson | 128/207.18 |
| 5,851,177 A * | 12/1998 | Koch | 600/206 |
| 5,890,899 A | 4/1999 | Sclafani | |
| 5,927,276 A * | 7/1999 | Rodriguez | 128/207.17 |
| 6,203,471 B1 | 3/2001 | Akihiro | |
| 6,234,962 B1 * | 5/2001 | Williams | 600/243 |
| 6,270,512 B1 * | 8/2001 | Rittmann | 606/199 |
| 6,500,002 B2 * | 12/2002 | Horiguchi | 433/140 |
| 6,743,017 B2 | 6/2004 | O'Neill | |
| 7,077,652 B2 | 7/2006 | Kilcher et al. | |
| 7,300,401 B2 | 11/2007 | Patrickus | |
| 7,607,917 B2 * | 10/2009 | Virnicchi et al. | 433/29 |
| 7,985,180 B2 * | 7/2011 | Brown | 600/236 |
| 2002/0022211 A1 * | 2/2002 | Horiguchi | 433/140 |
| 2004/0072126 A1 * | 4/2004 | Horvath | 433/138 |
| 2005/0171406 A1 * | 8/2005 | Dorfman | 600/237 |
| 2006/0063979 A1 * | 3/2006 | Rosenblood et al. | 600/237 |
| 2006/0069316 A1 | 3/2006 | Dorfman et al. | |
| 2006/0135853 A1 * | 6/2006 | Chin | 600/242 |
| 2006/0234187 A1 | 10/2006 | Kilcher et al. | |
| 2007/0218422 A1 | 9/2007 | Ehrenfeld | |
| 2007/0231773 A1 * | 10/2007 | Pontynen et al. | 433/140 |
| 2007/0293730 A1 * | 12/2007 | Rioux et al. | 600/215 |
| 2008/0064001 A1 | 3/2008 | Dorfman et al. | |
| 2008/0153058 A1 | 6/2008 | Horvath | |
| 2009/0081611 A1 | 3/2009 | Hines et al. | |
| 2010/0203466 A1 * | 8/2010 | Lawrence | 433/29 |
| 2010/0217090 A1 * | 8/2010 | Heiges et al. | 600/217 |
| 2010/0297579 A1 | 11/2010 | Beloff | |
| 2011/0060194 A1 * | 3/2011 | Risto et al. | 600/210 |

FOREIGN PATENT DOCUMENTS

| | | |
|---|---|---|
| DE | 4121804 A1 * | 1/1993 |
| DE | 10023863 A1 * | 11/2001 |
| EP | 884022 A2 * | 12/1998 |
| EP | 1336420 A2 * | 8/2003 |
| GB | 2048076 A * | 12/1980 |
| GB | 2143437 A * | 2/1985 |
| JP | 10137267 A * | 5/1998 |
| JP | 11178792 A * | 7/1999 |
| JP | 2006326017 A * | 12/2006 |
| WO | WO 9629952 A1 * | 10/1996 |

\* cited by examiner

ORAL RETRACTOR

BACKGROUND OF THE INVENTION

1. Field of the Invention

The present invention relates to a dental instruments, and particularly to an oral retractor for retracting a patient's lips and cheeks during dental and orthodontic procedures.

2. Description of the Related Art

Oral retractors for retracting a patient's lips and checks during dental and orthodontic procedures are well known. Typical retractors are formed from a variety of differing parts, often formed from a combination of surgical stainless steel and plastic. The retractors typically require assembly and adjustment of a wide variety of complex pieces. Further, the parts, which are not formed from surgical stainless steel alone, are difficult to sterilize.

Sterilization typically takes place in an autoclave at a temperature of above 130° C. Plastics and other materials cannot be sterilized in the autoclave and must be washed separately. Since regular washing is not as effective, cross contamination is an obvious concern with such retractors.

Thus, an oral retractor solving the aforementioned problems is desired.

SUMMARY OF THE INVENTION

The oral retractor is provided for retracting at least a portion of a patient's mouth. The oral retractor is formed from single, continuous closed-loop strand of wire, such as surgical stainless steel or the like. The oral retractor includes a pair of longitudinally opposed lip-engaging portions and a pair of laterally opposed cheek-engaging portions. Each cheek-engaging portion has a substantially parabolic shape and a pair of longitudinally opposed ends.

Each lip-engaging portion includes a pair of substantially linear portions defining a central angled peak that extends anteriorly. The superior lip-engaging portion may slope slightly upward, and the inferior lip-engaging portion may slope slightly downward. The lip engaging portions also include a pair of longitudinally extending links, medially extending members that join the cheek-engaging portions.

Each of the check-engaging portions define arcuate or parabolic shapes that extend posteriorly and laterally outward. The lip-engaging portions retract the upper and lower lips away from the teeth and gums, and the cheek-engaging members retract the cheeks outward to provide the dentist or orthodontist access to the patient's teeth and gums These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
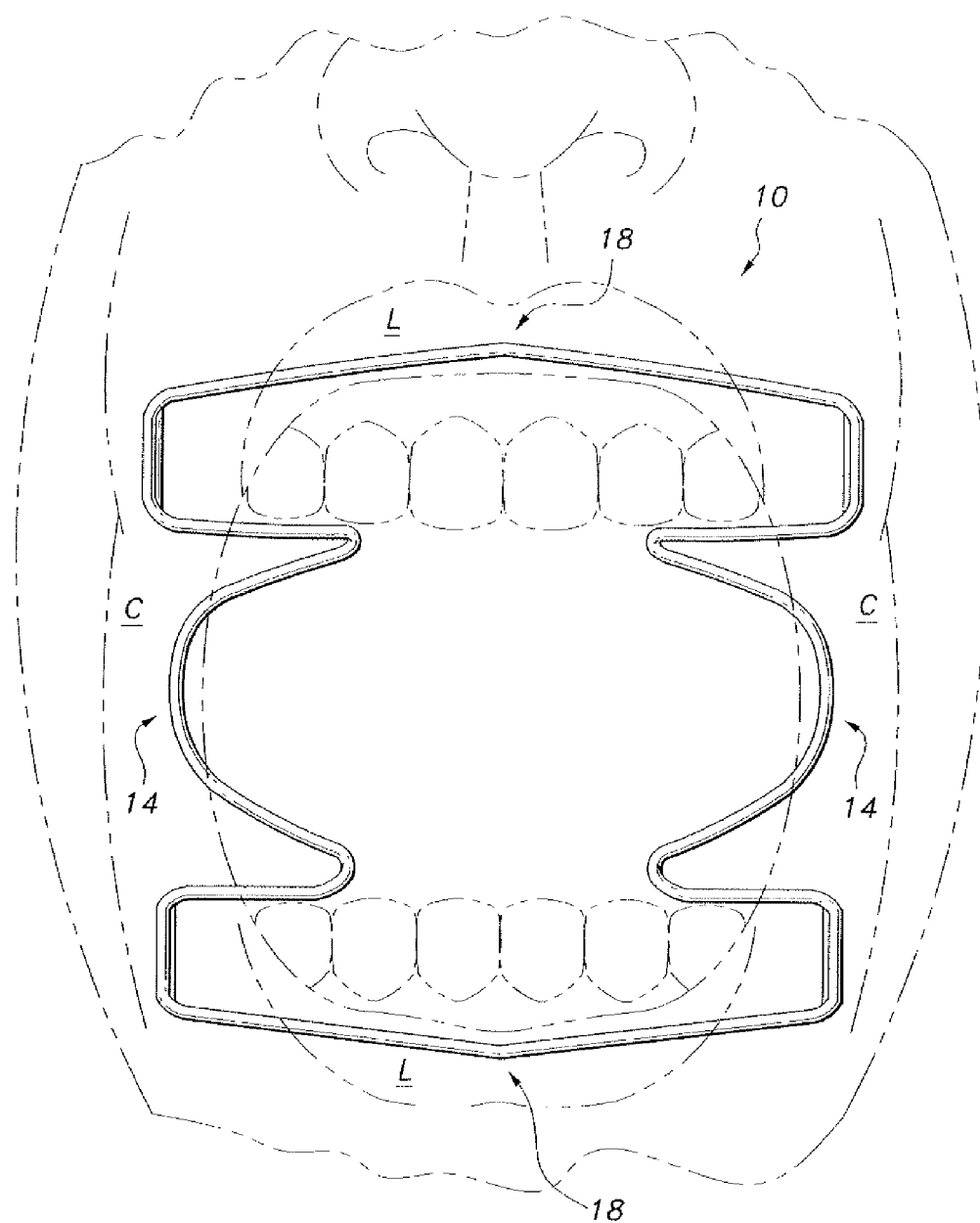
FIG. 1 is an environmental front view of an oral retractor according to the present invention.

As best shown in FIG. 1, the oral retractor 10 is provided for retracting at least a portion of a patient's mouth for oral procedures, such as the bonding of orthodontic brackets to the teeth T. As shown in FIG. 1, the oral retractor retracts both the patient's lips L and cheeks C, exposing the teeth T to the dental or orthodontic practitioner. The oral retractor 10 is formed from single, continuous closed-loop strand of wire, such as surgical stainless steel 443, surgical stainless steel 335 or the like. In order to minimize discomfort for the patient, the wire forming the oral retractor is preferably relatively thin and lightweight, such as a single strand of surgical stainless steel having a diameter of approximately 3 mm.

Figure 2:
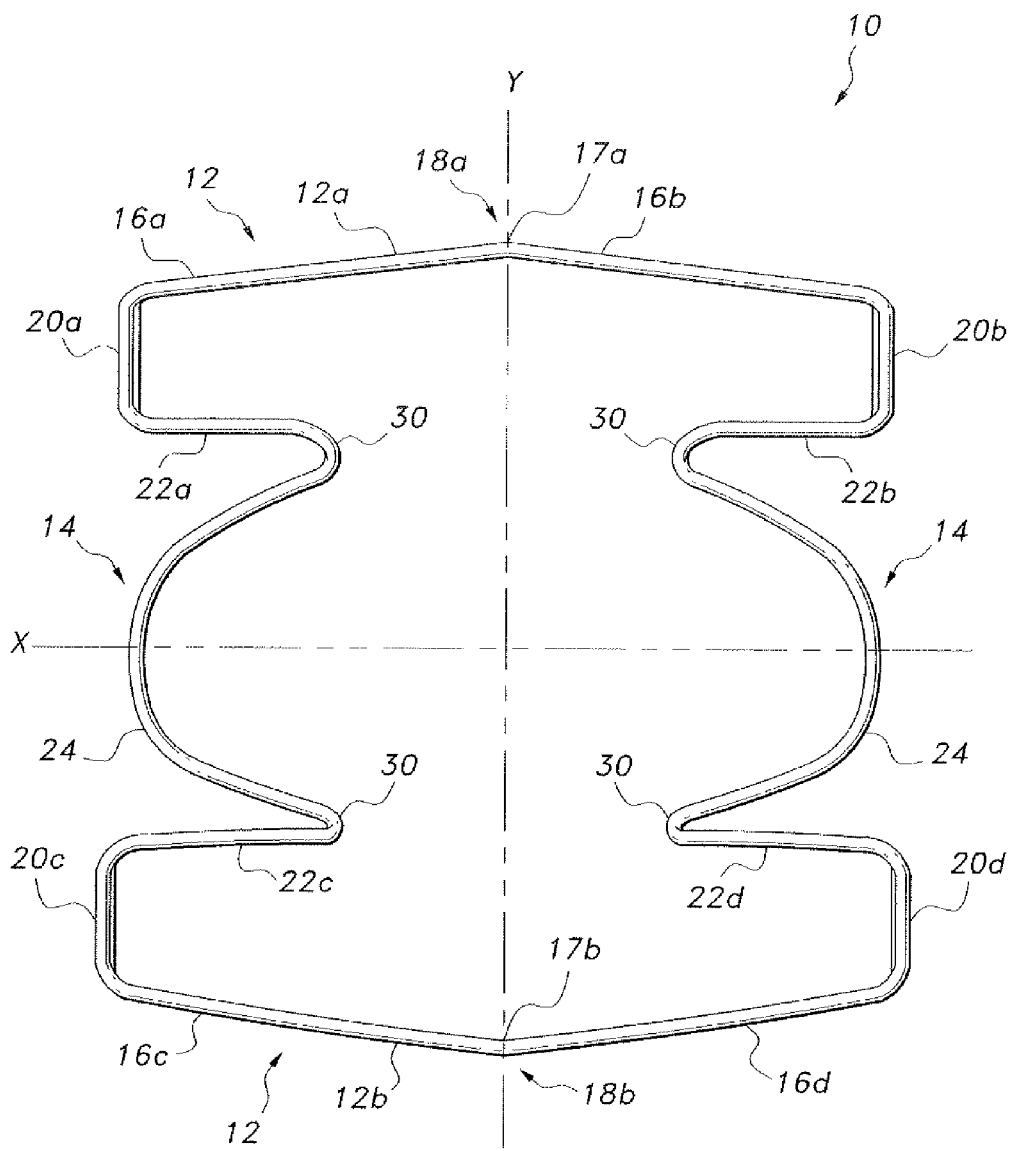
FIG. 2 is a front view of the oral retractor according to the present invention.

As best shown in FIG. 2, the oral retractor 10 includes a pair of longitudinally opposed (i.e., superior 12a and inferior 12b) lip-engaging portions 12 and a pair of laterally opposed cheek-engaging portions 14. The oral retractor 10 is preferably symmetrical about a lateral axis x, and also about a longitudinal axis y. Each cheek-engaging portion 14 has a substantially parabolic shape and a pair of longitudinally opposed ends (i.e., a superior end and an inferior end). The portion of the overall, single continuous wire strand forming the substantially parabolic cheek-engaging portion 14 is designated as 24 in FIG. 2.

Each lip-engaging portion 12 includes first and second laterally extending linear portions 16a, 16b, and 16c, 16d joined at vertices 17a and 17b, respectively, to define central angled peaks 18a, 18b. Each lip-engaging portion 12 further includes a pair of longitudinally extending links 20a, 20b and 20c, 20d, respectively, the links 20a and 20b being substantially parallel to each other and extending inferiorly from the ends of linear portions 16a and 16b, respectively, while the links 20e and 20d are substantially parallel to each other and extend superiorly from opposite ends of the linear portions 16c and 16d, respectively, the links 20a, 20b, 20c, and 20d being substantially co-planar. Each lip-engaging portion 12 also includes third and fourth medially extending members 22a, 22b and 22c, 22d, which extend medially from the opposite ends of the corresponding links 20a, 20b, 20c, and 20d, the third and fourth medially extending members 22a, 22b, 22c, and 22d being shorter than the corresponding laterally extending linear portions 16a, 16b, 16e, and 16d.

Figure 5:
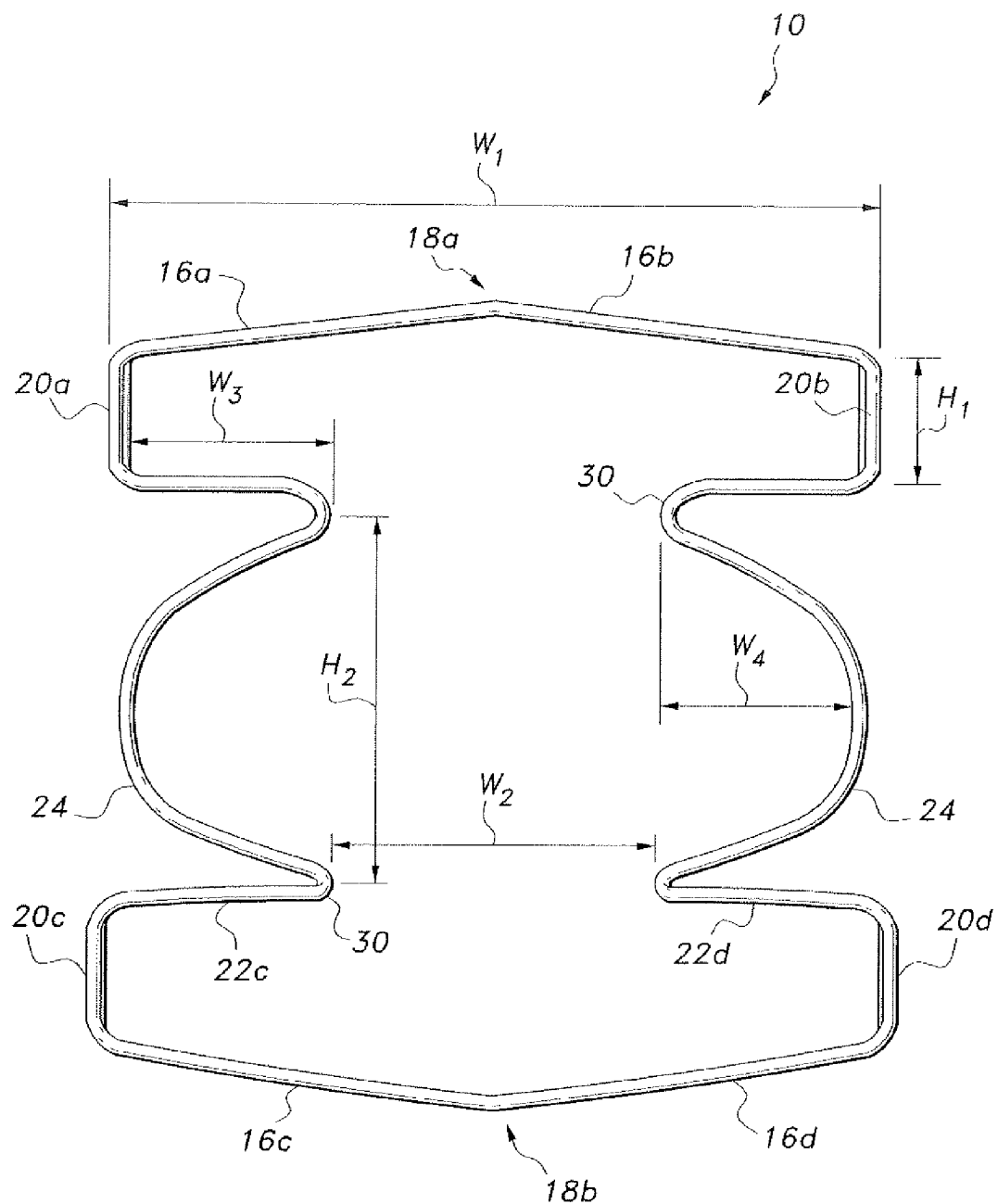
FIG. 5 is a front view of the oral retractor of FIG. 1, illustrating exemplary relative dimensions thereof.

Each of the longitudinally opposed ends of the check engaging portions 14 is secured to a respective second end of a corresponding one of the medially extending members 22a, 22b, 22c, and 22d (the junctions being designated as 30 in FIG. 2), the portion of the stainless steel wire between the medially extending members 22a, 22b, 22c, 22 and the cheek extending members 14 being bent or formed into a loop to define the junctions 30. It should be understood that the oral retractor 10 may have any desired relative dimensions, depending upon the particular size and shape of the patient's mouth. With reference to FIG. 5, exemplary dimensions include a first lateral width $W_1$ between laterally opposed links 20a, 20b and 20c, 20d of approximately 10 cm, a second lateral width $W_2$ between laterally opposed junctions 30 of approximately 5 cm, a third lateral width $W_3$ of each medially extending member 22a, 22b, 22e, and 22d of approximately 3 cm, a fourth lateral width $W_4$ defining the overall width of each cheek-engaging member 14 (i.e., the lateral distance between junction points 30 of each cheek engaging member 24 and its corresponding lateral peak) of approximately 4 cm, a first longitudinal height $H_1$ defining the length of each link 20a, 20b, 20c, and 20d of approximately 2 cm, and a second longitudinal height $H_2$ of each cheek-engaging portion 14

(i.e., the distance between longitudinally opposed junction points 30 of each cheek-engaging portion 14) of approximately 5 µm.

Figure 3:
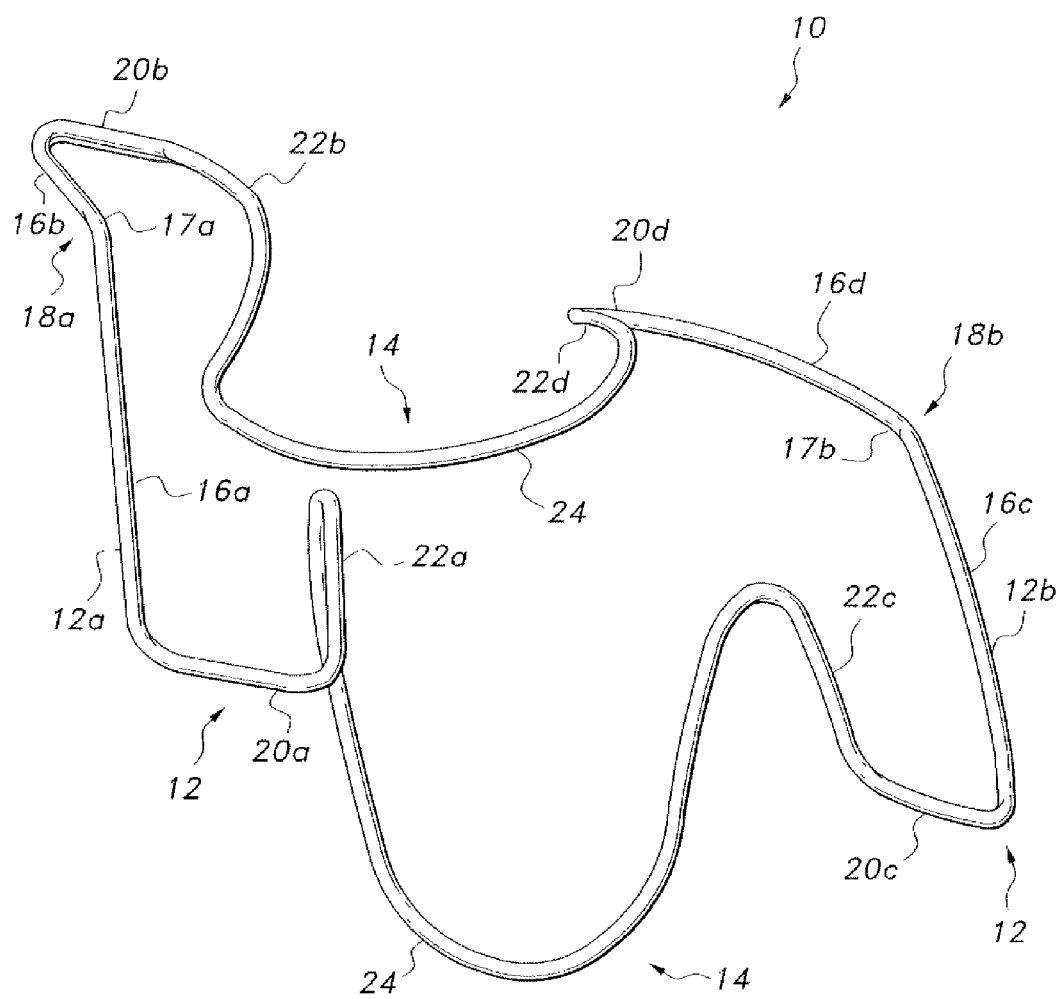
FIG. 3 is a perspective view of the oral retractor according to the present invention as seen from the side.
Figure 4:
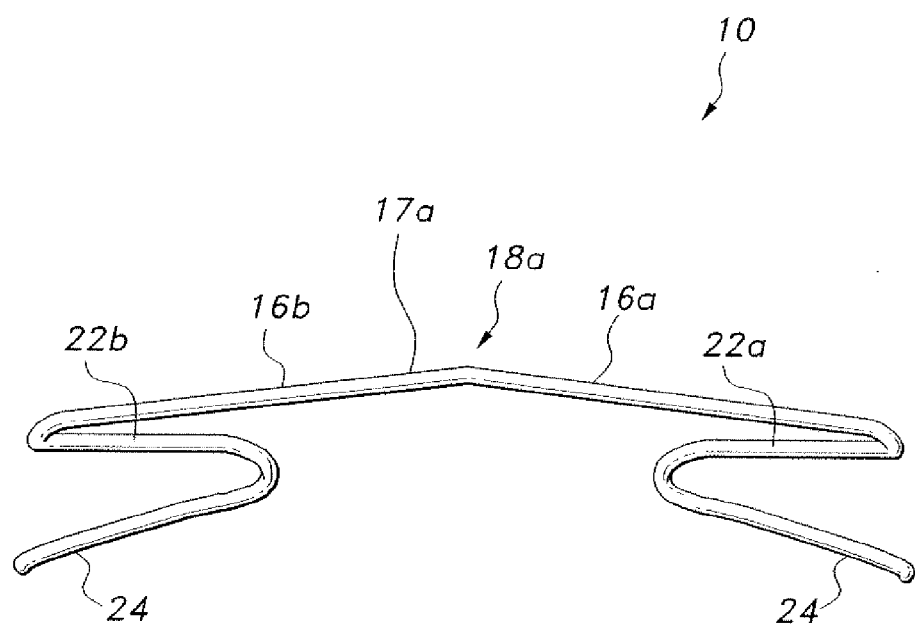
FIG. 4 is an end view of the oral retractor according to the present invention.

As best shown in FIGS. 2, 3 and 4, the superior lip-engaging portion 12a extends anteriorly from the links 20a, 20b, and the linear portions 16a, 16b may also be canted or slope slightly upward, so that the angled peak 18a forms a tented arch to retract the patient's upper lip away from the gums and upper teeth and slightly upward to expose the teeth. Similarly, the inferior lip-engaging portion 12b extends anteriorly from the links 20c, 20d, and the linear portions 16c, 16d may also be canted or slope slightly downward, so that the angled peak 18b forms a tented arch to retract the patient's lower lip away from the gums and lower teeth and slightly downward to expose the teeth. The bilateral cheek-engaging portions 14 both extend posterior to the links 20a, 20b, 20c, 20d and extend laterally or outward from the links 20a, 20b, 20c, and 20d in order to retract the patient's cheeks outward and away from the teeth and gums to provide the dentist or orthodontist access to the mouth for performing the procedure. Preferably, the angled peaks 18a, 18b and the vertices 17a, 17b are each at least slightly rounded to provide the patient with further comfort. Whereas currently available retractors are made from plastic, the oral retractor 10 is made from stainless steel, permitting sterilization by autoclave.

It is to be understood that the present invention is not limited to the embodiments described above, but encompasses any and all embodiments within the scope of the following claims.

I claim:

1. An oral retractor, comprising:
    a superior lip-engaging portion adapted for retracting a patient's upper lip from the patient's upper teeth and gums, the superior lip-engaging portion having:
        a pair of laterally extending linear portions joined at an angle to form a tented arch having laterally extending ends;
        a pair of superior links extending longitudinally downward from the laterally extending ends to opposite ends, the superior links being parallel to each other; and
        a pair of medially extending portions extending from the opposite ends of the superior links;
    an inferior lip-engaging portion adapted for retracting a patient's lower lip from the patient's lower teeth and gums, the inferior lip-engaging portion having:
        a pair of laterally extending linear portions joined at an angle to form a tented arch having laterally extending ends;
        a pair of inferior links extending longitudinally upward from the laterally extending ends to opposite ends, the inferior links being parallel to each other and substantially co-planar with the superior links; and
        a pair of medially extending portions extending from the opposite ends of the inferior links; and
    a pair of bilateral arcuate cheek-engaging portions adapted for retracting the patient's cheeks away from the patient's teeth and gums, the cheek-engaging portions extending between the medially extending portions of the superior lip-engaging portion and the medially extending portions of the inferior lip-engaging portions, the cheek-engaging portions extending posteriorly and laterally from the superior and inferior links, the superior and inferior lip-engaging portions extending anteriorly from the superior and inferior links.

2. The oral retractor as recited in claim 1, wherein said oral retractor is a stainless steel wire defining a continuous, closed loop, whereby the oral retractor has a wireframe body.

3. The oral retractor as recited in claim 1, wherein said oral retractor is symmetrical about a longitudinal plane bisecting the superior and inferior tented arches, and is also symmetrical about a transverse plane bisecting the arcuate cheek portions.

4. The oral retractor as recited in claim 1, wherein said superior lip-engaging portion slopes upward.

5. The oral retractor as recited in claim 4, wherein said inferior lip-engaging portion slopes downward.

6. The oral retractor as recited in claim 1, wherein each said arcuate cheek-engaging portion is substantially parabolic.

7. An oral retractor, comprising a single stainless steel wire defining a continuous, closed loop, the loop defining a wireframe body having:
    a superior lip-engaging portion adapted for retracting a patient's upper lip from the patient's upper teeth and gums, the superior lip-engaging portion having:
        a pair of laterally extending linear portions joined at an angle to form a tented arch having laterally extending ends;
        a pair of superior links extending longitudinally downward from the laterally extending ends to opposite ends, the superior links being parallel to each other; and
        a pair of medially extending portions extending from the opposite ends of the superior links;
    an inferior lip-engaging portion adapted for retracting a patient's lower lip from the patient's lower teeth and gums, the inferior lip-engaging portion having:
        a pair of laterally extending linear portions joined at an angle to form a tented arch having laterally extending ends;
        a pair of inferior links extending longitudinally upward from the laterally extending ends to opposite ends, the inferior links being parallel to each other and substantially co-planar with the superior links; and
        a pair of medially extending portions extending from the opposite ends of the inferior links; and
    a pair of bilateral arcuate cheek-engaging portions adapted for retracting the patient's cheeks away from the patient's teeth and gums, the cheek-engaging portions extending between the medially extending portions of the superior lip-engaging portion and the medially extending portions of the inferior lip-engaging portions, the cheek-engaging portions extending posteriorly and laterally from the superior and inferior links, the superior and inferior lip-engaging portions extending anteriorly from the superior and inferior links.

8. The oral retractor as recited in claim 7, wherein said oral retractor is symmetrical about a longitudinal plane bisecting the superior and inferior tented arches, and is also symmetrical about a transverse plane bisecting the arcuate cheek portions.

9. The oral retractor as recited in claim 8, wherein said superior lip-engaging portion slopes upward.

10. The oral retractor as recited in claim 9, wherein said inferior lip-engaging portion slopes downward.

11. The oral retractor as recited in claim 7, wherein each said arcuate cheek-engaging portion is substantially parabolic.

12. An oral retractor, comprising:
    a superior lip-engaging portion adapted for retracting a patient's upper lip from the patient's upper teeth and gums, the superior lip-engaging portion having:

a pair of laterally extending linear portions joined at an angle to form a tented arch having laterally extending ends;

a pair of superior links extending longitudinally downward from the laterally extending ends to opposite ends, the superior links being parallel to each other; and a pair of medially extending portions extending from the opposite ends of the superior links;

an inferior lip-engaging portion adapted for retracting a patient's lower lip from the patient's lower teeth and gums, the inferior lip-engaging portion having:

a pair of laterally extending linear portions joined at an angle to form a tented arch having laterally extending ends;

a pair of inferior links extending longitudinally upward from the laterally extending ends to opposite ends, the inferior links being parallel to each other and substantially co-planar with the superior links; and a pair of medially extending portions extending from the opposite ends of the inferior links; and a pair of bilateral arcuate cheek-engaging portions adapted for retracting the patient's cheeks away from the patient's teeth and gums, the cheek-engaging portions extending between the medially extending portions of the superior lip-engaging portion and the medially extending portions of the inferior lip-engaging portions, the cheek-engaging portions extending posteriorly and laterally from the superior and inferior links, the superior and inferior lip-engaging portions extending anteriorly from the superior and inferior links, the superior lip-engaging portion extending upward from the superior links, the inferior lip-engaging portion extending downward from the inferior links.

13. The oral retractor as recited in claim 12, wherein said oral retractor is a stainless steel wire defining a continuous, closed loop, whereby the oral retractor has a wireframe body.

14. The oral retractor as recited in claim 12, wherein said oral retractor is symmetrical about a longitudinal plane bisecting the superior and inferior tented arches, and is also symmetrical about a transverse plane bisecting the arcuate cheek portions.

15. The oral retractor as recited in claim 12, wherein each said arcuate cheek-engaging portion is substantially parabolic.

* * * * *